United States Patent [19]

McDermed et al.

[11] 4,064,271

[45] Dec. 20, 1977

[54] EMETIC TETRALONES AND THE USE THEREOF FOR INDUCING REGURGITATION

[75] Inventors: John D. McDermed, Durham; Gerald M. McKenzie; Arthur P. Phillips, both of Raleigh, all of N.C.

[73] Assignee: Burroughs Wellcome Co., Research Triangle Park, N.C.

[21] Appl. No.: 649,686

[22] Filed: Jan. 16, 1976

Related U.S. Application Data

[62] Division of Ser. No. 455,789, March 28, 1974, abandoned.

[51] Int. Cl.$^2$ .................... A61K 31/135; C07C 91/16; C07C 91/28
[52] U.S. Cl. .................................... 424/330; 260/574
[58] Field of Search .................... 424/330; 260/574

[56] References Cited

U.S. PATENT DOCUMENTS

| 2,632,024 | 3/1953 | Grob | 260/590 |
|---|---|---|---|
| 3,574,762 | 4/1971 | Nagato et al. | 260/590 |

OTHER PUBLICATIONS

J. D. McDermed et al., J. Med. Chem. 18, 362 (1975).
Cannon, et al., Journal of Med. Chem. 1972, vol. 15, No. 4, pp. 348–350.
W. K. Sprenger et al., Journal of Med. Chem. vol. 12, pp. 487–490 May 1969.
J. G. Cannon et al., J. Het. Chem. Aug. 1972, pp. 959–962.

*Primary Examiner*—Stanley J. Friedman
*Attorney, Agent, or Firm*—Donald Brown

[57] ABSTRACT

5,6-Dialkoxy-2-tetralones (I) are disclosed as useful intermediates in the synthesis of 2-amino-5,6-dialkoxytetralins (III) and 2-amino-5,6-dihydroxytetralins (IV). Compounds of the groups III and IV are potent emetics.

12 Claims, No Drawings

EMETIC TETRALONES AND THE USE THEREOF FOR INDUCING REGURGITATION

This is a division, of application Ser. No. 455,789 filed Mar. 28, 1974, now abandoned.

This invention relates to certain β-tetralones useful as chemical intermediates and to the emetic 2-aminotetralins prepared therefrom.

Certain 2-amino-5,6-dimethoxytetralins have been reported to have emetic activity. Emetics are useful for quickly inducing regurgitation, i.e. vomiting, to empty the stomach, for example, after certain toxic materials have been ingested. Potent emetics may also be incorporated into certain formulations to prevent accidental poisonings by ingestion, e.g. by small children, of said formulations. Similarly, emetics may be incorporated into pharmaceutical formulations of medicinals which might be prone to misuse to induce emesis whenever an overdose was taken.

However, the synthetic routes available to the 2-amino-5,6-dialkoxytetralins have been inconvenient ones. The applicants have now discovered a novel class of intermediates useful in the synthesis of these 2-amino-5,6-dialkoxytetralins and methods for preparing these intermediates.

The novel intermediates of this invention are β-tetralones and have the general formula I wherein R and R' may be the same or different and each is lower alkyl preferably containing 1 to 8 carbon atoms and more preferably containing 1 to 4 carbon atoms.

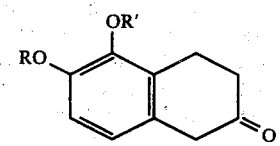

I

Compounds of formula I may be converted into the emetic 2-amino-5,6-dialkoxytetralins by condensation with suitably substituted amines to give enamine intermediates of formula II which may then be reduced to the desired compounds of formula III as shown in Scheme 1, wherein R" and R'" may be the same or different and each is H or lower alkyl preferably containing Scheme 1

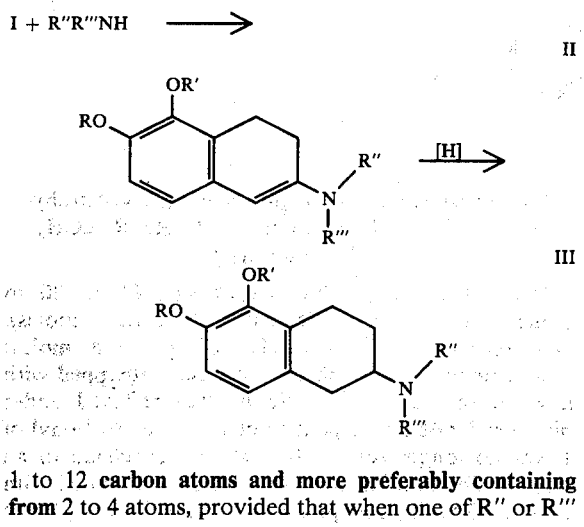

1 to 12 carbon atoms and more preferably containing from 2 to 4 atoms, provided that when one of R" or R'" is H or CH$_3$ the other is lower alkyl containing 2 to 12 carbon atoms. The compounds of formula III wherein R and R' are lower alkyl containing 2 to 8 carbon atoms are novel, and the compounds of formula III wherein R" and R'" are lower alkyl containing 2 to 12 carbon atoms are also novel.

Compounds of formula III may be converted into even more potent emetics by hydrolytic cleavage of the ether groups, e..g. by the action of Hi in acetic acid, to compounds having the general formula IV.

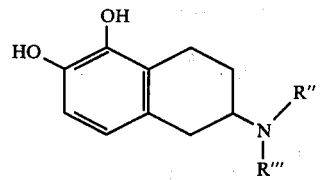

IV

The compounds of formula IV wherein R" and R'" are H or lower alkyl containing 1 to 12 carbon atoms, preferably 2 to 4 carbon atoms, provided that when one of R" or R'" is H or CH$_3$ the other is lower alkyl containing 2 to 12 carbon atoms are novel.

The emetics of formulas III and IV are administered to mannals to induce regurgitation, preferably as their salts, e.t. salts of the free bases with pharmaceutically acceptable acids. The preferred method of administration is orally in any of the well-known pharmaceutical forms such as tablets, capsules, cachets, elixirs, etc. Administration may also be by injectionk, preferably intramuscularly or more preferably intravenously, of a solution, preferably aqueous, of the compounds of formulas III and IV, preferably as their water-soluble salts with pharmaceutically acceptable acids. Pharmaceutically acceptable carriers and other excipients well known in the art may be used in the formulation of pharmaceutical preparations.

A suitable, effective dosageto induce regurgitation in mammals of compounds of formula III and IV would be within the range 0.1 to 1000 mg/kg of body weight, preferably 0.2 to 100 mg/kg.

The emetic potencies of representative compounds of formulas III and IV in dogs (administered as aqueous solutions of the hydrochloride salts by intramuscular injection) are given in Table A and compared with the known emetic apomorphine.

Table A

| Emetic Potency of Certain 2-Aminotetralin Hydrochlorides | | | | | | |
|---|---|---|---|---|---|---|
| Compound | Formula | R | R' | R" | R'" | Em* |
| 1 | III | CH$_3$ | CH$_3$ | C$_2$H$_5$ | C$_2$H$_5$ | 440 |
| 2 | III | CH$_3$ | CH$_3$ | CH$_3$ | C$_3$H$_7$-n | 880 |
| 3 | IV | — | — | C$_2$H$_5$ | C$_2$H$_5$ | 0.48 |
| 4 | IV | — | — | C$_3$H$_7$-n | C$_3$H$_7$-n | 0.57 |
| Apomorphine | | | | | | 26 |

*Em is the smallest dose (μg/kg of body weight, reported as the free base) at which emesis occurs.

Compounds of formula I may be prepared most conveniently from the chemical reduction, e.g. by sodium in ethanol, of the appropriate 1,2,6-trialkoxynaphthalene, followed by acidification. Other alkali metals, e.g. potassium or lithium, could be used in a number of other solvents, such as higher alcohols, liquid ammonia, lower primary or secondary amines, or mixtures of amines and alcohols to effect the reduction step.

Alternatively compounds of formula I may be prepared from compounds of formula V by oxidation, e.g. with CrO₃ in acetic acid, of the alcohol to a ketone. Compounds of formula I may be prepared from dihydronaphthalenes of formula VI, for example, by epoxidation to the oxirane VII followed by treatment with boron trifluoride etherate in ether. Alternatively VI may be hydrated to give V by reaction with diborane followed by treatment with basic hydrogen peroxide.

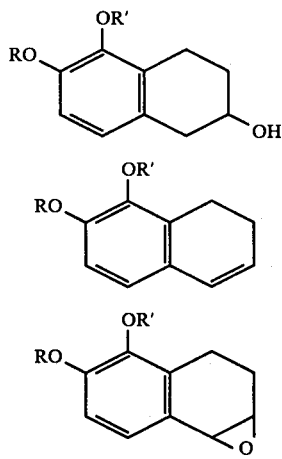

1,2,6-Trialkoxynaphthalene may be prepared from 2,6-dihydroxynaphthalene according to Scheme 2 which involves an initial reaction with Fremy's radical ]·O-N(SO₃K)₂] in a buffered medium of pH 3-5 to give VIII which is then reduced, preferably in DMF, with e.g. sodium dithionite to give 1,2,6-trihydroxynaphthalene. This compound is very sensitive to air oxidation and is preferably alkylated without isolation, for example by dimethylsulfate to give 1,2,6-trimethoxynaphthalene.

suspension was refluxed for 30 minutes. After cooling, sufficient water was added to dissolve the solid present. Extraction with methylene chloride followed by drying and evaporation of the solvent yielded I as a viscous oil. This oil was shaken with saturated NaHSO₃ solution (75 ml.) to form the bisulphite adduct of I. After 30 minutes the adduct was collected by filtration and washed, first with ethanol and then with ether, yielding 5.2 g. (17 m mole, 73%) of white powder. The free, purified ketone, m.p. 50° C., was obtained as needed by adding the bisulphite adduct to a stirred mixture of ether and excess 10% aqueous Na₂CO₃ solution, followed by separating, washing, drying, and evaporating the other layer.

EXAMPLE 2

5,6-Dimethoxy-2-diethylamino-1,2,3,4-tetrahydronaphthalene hydrochloride (III, R=R'=CH₃; R''=R'''= C₂H₅)

Compound I, R=R'=CH₃ (2.8 g., 13.6 m moles), diethylamine (6 g., 82 m moles), 5 A molecular sieves (5 g.), and p-toluenesulfonic acid monohydrate (0.2 g., 1 m mole) were combined in benzene (75 ml.) under nitrogen in a pressure bottle. The bottle was stoppered, clamped shut and heated in a steam bath for 3 days. After cooling, the bottle was opened, the molecular sieves were removed and rinsed with ethanol (75 ml.). Platinum oxide (150 mg.) was added to the combined filtrate. Hydrogenation was performed on a Parr apparatus just above atmospheric pressure. The theoretical amount of hydrogen was absorbed in 45 minutes. Removal of catalyst and evaporation of the solvent left 3.4 g. of a dark oil, which was chromatographed on a column of activity I alumina (38 g.) eluting with 85% hexane/15% benzene. This produced the pure amine as an oil (2.8 g., 79%. The hydrochloride was obtained by dissolution in a little HCl/methanol and trituration with ethyl acetate, m.p. 177°-179° C.

EXAMPLE 3

Scheme 2

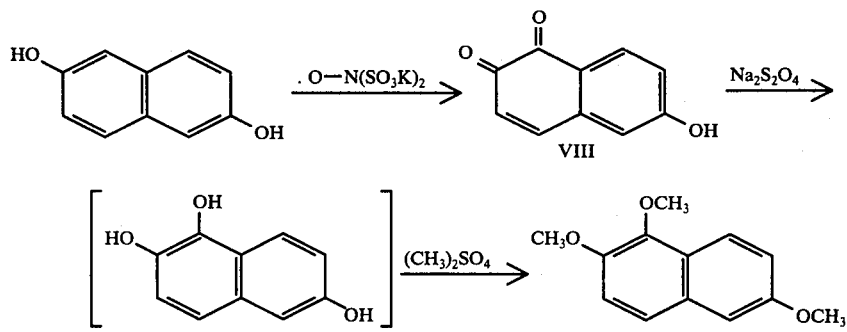

The following examples illustrate but should not be construed to limit the invention.

EXAMPLE 1

3,4-Dihydro-5,6-dimethoxy-2(1H)-naphthalenone (I, R=R'' = CH₃)

1,2,6-Trimethoxynaphthalene (5.0 g.; 23 m mol) was dissolved in ethanol (55 ml.). Under nitrogen, sodium metal (5.5 g; 240 m mol) was added in small pieces at a rate adequate to maintain refluxing. After all this sodium was added, the flask was heated to reflux until all the metal was dissolved. After cooling slightly, water (20 ml.) was added down the condenser followed cautiously by concentrated HCl (40 ml.). The resulting 5,6-Dimethoxy-2-di-n-propylamino-1,2,3,4,-tetrahydronaphthalene hydrochloride (III, R=R'=CH₃; R'''= n-C₃H₇)

Benzene (50 ml.), di-n-propylamine (2 g., 20 m moles), p-toluenesulphonic acid (0.25 g., 1.5 m moles), and compound I, R=R'=CH₃ (1.3 g., 6.3 m moles) were combined under nitrogen in a flask equipped with a water separator. The solution was refluxed under nitrogen for 48 hours, after which time the carbonyl of I was no longer seen in the infrared spectrum of an aliquot. The solution was then cooled and diluted with ethanol (50 ml.), and platinum dioxide (100 mg.) was added. Hydrogenation of the reaction mixture was accomplished in a Parr apparatus just above atmospheric pressure. The theoretical amount of hydrogen was taken up within 30 minutes. Removal of the catalyst and evaporation of the solvent yielded a crude dark oil. This was passed through a short column of activity I alumina (20 g.), eluting with 80% hexane/20% benzene, which yielded the pure amine as a colourless oil (1.4 g., 77%). The hydrochloride was obtained by solution of the free amine in hydrogen chloride/methanol and trituration in hot ethyl acetate, m.p. 178°–179° C.

EXAMPLE 4

5,6-Dihydroxy-2-diethylamino-1,2,3,4-tetrahydronaphthalene hydroiodide (IV, R''=R'''= $C_2H_5$)

Under nitrogen at 0° C, 47% HI solution (2.6 g., 9.5 m moles HI, 76.5 m moles $H_2O$) was added to near 5,6-dimethoxy-2-diethylamino-1,2,3,4-tetrahydronaphthalene 0.4 g., 1.5 m moles), followed by dropwise addition of acetic anhydride (7.1 g., 69.5 m moles). This was heated at gentle reflux for 50 minutes. Ethyl acetate (12 ml.) was added and the resulting suspension was cooled to 0° C and filtered, yielding 0.35 g. of a yellow crystalline solid. This was recrystallized from acetic acid-/ethyl acetate to give 0.25 g. (45%) of the pure, colourless hydroiodide salt m.p. 174°–175° C

EXAMPLE 5

5,6-Dihydroxy-2-di-n-propylamino-1,2,3,4-tetrahydronaphthalene hydroiodide (IV, R''=R'''= $N-C_3H_7$)

Following the procedure of Example 4 except that the product of Example 3 used instead of that of Example 2, IV (R'=R''' = $n-C_3H_7$) was prepared as the hydroiodide salt in 65% yield, m.p. 208° C. (dec.).

EXAMPLE 6

5,6-Dimethoxy-2-n-propylamino-1,2,3,4-tetrahydronaphthalene hydrochloride (III, R=R' = $CH_3$; R''= H; R'''= n -$C_3H_7$)

Under nitrogen compound I, R=R' = $CH_3$ (1.4 g., 6.8 m moles) and n-propylamine (2.1 g., 35.6 m moles) were dissolved in ethanol (50 ml.) in a Parr hydrogenation bottle. Platinum dioxide (150 mg.) was added and hydrogenation was performed just above atmospheric pressure. The theoretical uptake of hydrogen was complete within 2 hours. Removal of catalyst and evaporation of all solvent left 1.6 g. of a brown oil. This was dissolved in dilute aqueous HCl and washed with benzene, which was discarded. The acid solution was neutralized with excess KOH, and the liberated amine was extracted into $CH_2Cl_2$, which was subsequently evaporated, leaving 1.15 g. of slightly colored oily amine. This was decolorized by elution with benzene through a short column of activity III alumina (6 g.). The purified oily amine (1.1 g., 65%) was converted to its HCl salt, m.p. 227°–229° C, by dissolution in HCl/ethanol and addition of ether.

EXAMPLE 7

5,6-Dimethoxy-2-(N-methyl-N-n-propylamino)-1,2,3,4-tetrahydronaphthalene hydrochloride (III, R=R' = $CH_3$; R''= $CH_3$; R'''= n-$C_3H_7$)

A solution of 5,6-tetrahydronaphthalene (1.25 G., 5 m moles), 37% formaldehyde solution (0.45 g., 5 m moles), and 90% formic acid (6 ml.) was heated on a steam bath under an air-cooled condenser for 1 hour. More 37% formaldehyde (0.1 g., 1.2 m moles) was added, and heating was continued an additional 2 hours. The reaction mixture was poured into excess aqueous KOH and the liberated amine extracted into $CH_2DL_2$. The oil obtained by evaporation of the $CH_2CL_2$ solvent was chromatographed on activity I alumina (20 g.), eluting with 90% hexane/10% ethyl acetate. This yielded 1.15 g, (89%) of pure oily amine which was converted to its HCl salt, m.p. 180°, by dissolution in HCl/methanol and addition of ethyl acetate.

EXAMPLES 8 – 10

Following the procedure of Example 4, the tablulated compounds of formula IV were prepared from the corresponding 5,6-dimethoxy compounds of formula III.

| Example | R'' | R''' | Yield, % | m.p., ° C |
| --- | --- | --- | --- | --- |
| 8 | n-$C_4H_9$ | n-$C_4H_9$ | 66 | 155–156.5 |
| 9 | H | n-$C_3H_7$ | 64 | 231–233 |
| 10 | H | n-$C_6H_{13}$ | 72 | 92–94 |

We claim:
1. A compound of formula

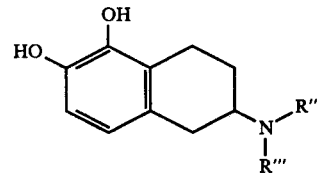

wherein R'' and R''' are the same or different and each is lower alkyl containing 2 or 3 carbon atoms or a pharmaceutically acceptable salt thereof.

2. A compound of the formula

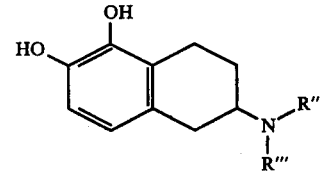

wherein R'' and R''' are ethyl or a pharmaceutically acceptable salt thereof.

3. A compound of the formula

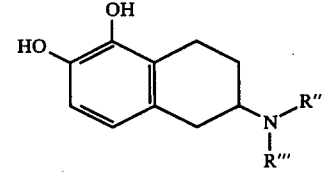

wherein R'' and R''' are n-propyl or a pharmaceutically acceptable salt thereof.

4. A compound of the formula

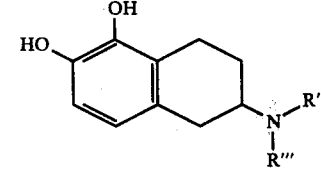

wherein R" is hydrogen and R'" is n-propyl or a pharmaceutically acceptable salt thereof.

5. A pharmaceutical composition for use in inducing regurgitation in mammals which comprises an effective non-toxic mammal regurgitation amount of the compound or salt of claim 1 and a pharmaceutically acceptable carrier therefore.

6. The pharmaceutical composition of claim 5 wherein R" and R'" are ethyl.

7. The pharmaceutical composition of claim 5 wherein R" and R'" are n-propyl.

8. A pharmaceutical composition for use in inducing regurgitation in mammals which comprises an effective non-toxic regurgitation amount of the compound or salt of claim 4 and a pharmaceutically acceptable carrier therefore.

9. A method for inducing regurgitation in a mammal which comprises administering to said mammal the pharmaceutical composition of claim 5.

10. The method of claim 9 wherein R" and R'" are ethyl.

11. The method of claim 9 wherein R" and R'" are n-propyl.

12. A method of inducing regurgitation in a mammal which comprises administering to said mammal the pharmaceutical composition of claim 8.

* * * * *